United States Patent [19]

Olsen

[11] Patent Number: 5,695,473
[45] Date of Patent: Dec. 9, 1997

[54] OCCLUSION DETECTION SYSTEM FOR AN INFUSION PUMP

[75] Inventor: James M. Olsen, Plymouth, Minn.

[73] Assignee: Sims Deltec, Inc., St. Paul, Minn.

[21] Appl. No.: 281,179

[22] Filed: Jul. 27, 1994

[51] Int. Cl.$^6$ .................................................. A61M 1/000
[52] U.S. Cl. ............................ 604/153; 128/DIG. 13
[58] Field of Search ............................ 604/65, 66, 67, 604/151, 153; 128/DIG. 12, DIG. 13

[56] References Cited

U.S. PATENT DOCUMENTS

| | | |
|---|---|---|
| Re. 31,315 | 7/1983 | Jenkins et al. |
| 3,603,152 | 9/1971 | Alibert et al. |
| 3,942,526 | 3/1976 | Wilder et al. |
| 3,963,702 | 6/1976 | Ferres et al. |
| 4,027,536 | 6/1977 | Heggie . |
| 4,141,252 | 2/1979 | Lodge . |
| 4,174,637 | 11/1979 | Mulzet et al. |
| 4,191,184 | 3/1980 | Carlisle . |
| 4,210,138 | 7/1980 | Jess et al. |
| 4,213,454 | 7/1980 | Shim . |
| 4,217,993 | 8/1980 | Jess et al. |
| 4,236,880 | 12/1980 | Archibald . |
| 4,270,532 | 6/1981 | Franetzki et al. |
| 4,279,188 | 7/1981 | Scott . |
| 4,299,218 | 11/1981 | Knigge et al. |
| 4,309,993 | 1/1982 | Brown . |
| 4,314,227 | 2/1982 | Eventoff . |
| 4,314,228 | 2/1982 | Eventoff . |
| 4,315,238 | 2/1982 | Eventoff . |
| 4,368,645 | 1/1983 | Glenn et al. |
| 4,369,780 | 1/1983 | Sakai . |
| 4,373,525 | 2/1983 | Kobayashi . |
| 4,385,630 | 5/1983 | Gilcher et al. |
| 4,394,862 | 7/1983 | Shim . |
| 4,395,259 | 7/1983 | Prestele et al. |
| 4,398,542 | 8/1983 | Cunningham et al. |
| 4,410,322 | 10/1983 | Archibald . |
| 4,431,425 | 2/1984 | Thompson et al. |
| 4,446,344 | 5/1984 | Fiedler . |
| 4,460,355 | 7/1984 | Layman . |
| 4,484,479 | 11/1984 | Eckhardt . |
| 4,489,302 | 12/1984 | Eventoff . |
| 4,493,704 | 1/1985 | Beard et al. |
| 4,520,706 | 6/1985 | Deforeit . |
| 4,526,574 | 7/1985 | Pekkarinen . |
| 4,530,696 | 7/1985 | Bisera et al. |
| 4,550,748 | 11/1985 | Nunez . |
| 4,559,038 | 12/1985 | Berg et al. |
| 4,563,179 | 1/1986 | Sakai . |
| 4,565,542 | 1/1986 | Berg . |
| 4,617,014 | 10/1986 | Cannon et al. |
| 4,624,661 | 11/1986 | Arimond . |
| 4,627,835 | 12/1986 | Fenton, Jr. |
| 4,685,903 | 8/1987 | Cable et al. |

(List continued on next page.)

FOREIGN PATENT DOCUMENTS

| | | |
|---|---|---|
| 0 049 350 | 1/1983 | European Pat. Off. |
| 0 371 507 B1 | 3/1993 | European Pat. Off. |
| 0 328 162 B1 | 12/1993 | European Pat. Off. |
| WO 91/16609 | 10/1991 | WIPO . |
| WO 95/25893 | 9/1995 | WIPO . |

OTHER PUBLICATIONS

"IV7000 Service Manual," Valleylab, Inc., Boulder Colorado; Sep., 1988.

*Primary Examiner*—Mark Bockelman
*Attorney, Agent, or Firm*—Merchant, Gould, Smith, Edell, Welter & Schmidt P.A.

[57] ABSTRACT

The invention relates to a method and system for monitoring pressure conditions in the fluid pressure upstream and downstream of an intravenous fluid administration system and to detect upstream and/or downstream occlusions. In addition, the invention incorporates a method for detecting pressure conditions at an upstream or downstream detector across the wall of the tubing to identify upstream or downstream occlusions, respectively. The present invention also relates to a process for determining the fluid pressure in a fluid tube across the tube wall where the normal tube force changes over time, and more particularly, using a normalization process to eliminate changes in the tubing resilience.

19 Claims, 11 Drawing Sheets

U.S. PATENT DOCUMENTS

| | | |
|---|---|---|
| 4,690,673 | 9/1987 | Bloomquist .................................. 604/67 |
| 4,702,765 | 10/1987 | Aldrovandi et al. . |
| 4,710,163 | 12/1987 | Butterfield . |
| 4,739,229 | 4/1988 | Heiler, Jr. . |
| 4,745,301 | 5/1988 | Michalchik . |
| 4,747,828 | 5/1988 | Tseo . |
| 4,774,029 | 9/1988 | Poulin . |
| 4,785,799 | 11/1988 | Schoon et al. . |
| 4,810,992 | 3/1989 | Eventoff . |
| 4,816,019 | 3/1989 | Kamen . |
| 4,836,752 | 6/1989 | Burkett . |
| 4,843,792 | 7/1989 | Bobo, Jr. et al. . |
| 4,852,581 | 8/1989 | Frank . |
| 4,863,425 | 9/1989 | Slate et al. . |
| 4,882,575 | 11/1989 | Kawahara et al. .......... 128/DIG. 13 X |
| 4,950,235 | 8/1990 | Slate et al. . |
| 4,976,151 | 12/1990 | Morishita . |
| 4,979,940 | 12/1990 | Bobo, Jr. et al. . |
| 4,994,035 | 2/1991 | Mokros . |
| 4,996,511 | 2/1991 | Ohkawa et al. . |
| 5,010,473 | 4/1991 | Jacobs . |
| 5,053,585 | 10/1991 | Yaniger . |
| 5,088,983 | 2/1992 | Burke . |
| 5,096,358 | 3/1992 | Georgi et al. ........................ 604/67 X |
| 5,096,385 | 3/1992 | Georgi et al. . |
| 5,103,211 | 4/1992 | Daoud et al. ........................ 604/67 X |
| 5,154,700 | 10/1992 | Danby . |
| 5,181,910 | 1/1993 | Scanlon . |
| 5,190,522 | 3/1993 | Wojcicki et al. . |
| 5,213,573 | 5/1993 | Sorich et al. ........................ 604/67 X |
| 5,217,355 | 6/1993 | Hyman et al. . |
| 5,356,378 | 10/1994 | Doan ........................................ 604/65 |
| 5,395,321 | 3/1995 | Kawahara et al. ...................... 604/67 |

OCCLUSION DETECTION SYSTEM FOR AN INFUSION PUMP

BACKGROUND OF THE INVENTION

Medical infusion pumps serve the needs of patients receiving intravenous, intramuscular or similar pharmaceutical therapy by delivering controlled amounts of fluid under pressurized flow conditions to the patients. Infusion pumps provide the additional advantage of being portable, allowing the patient to carry on normal activities while still maintaining his or her intravenous fluid administration regiment.

Infusion systems generally draw fluid from reservoirs through tubing. Additional segments of tubing are used to deliver the fluid from the infusion pump to the patient. Ideally, a continuous section of tubing extending from the fluid reservoir to the delivery needle is used to insure sterility.

If the tubing becomes occluded or partially occluded, the patient may be subject to an "under delivery" or "no delivery" situation. The problem of occlusion detection is further complicated in that many patients maintain and operate their own fluid administration regiment without the supervision of health care providers. Therefore, detecting occlusions in the fluid lines is important for safe and effective operation of the infusion pumps.

Occlusions may be of two kinds, upstream and downstream of the pump. Each has its own set of indications. Upstream occlusions may be detected by an upstream sensor monitoring pressure drop in the upstream tubing. In such situations, the "pull" of the infusion pump against the occlusion will produce up to a −10 psi pressure drop or partial vacuum relative to a baseline pressure of the system, the baseline being defined, and for the purposes of this invention is defined, as the system pressure present between pumping cycles when the system is operating in an un-occluded condition. This phenomenon has led to the technique disclosed in U.S. Pat. No. 5,096,385 (the '385 patent) to measure upstream occlusions in connection with a peristaltic infusion system.

In particular, the '385 patent discloses use of a downstream pressure sensor to detect negative going pressure transients and identify upstream occlusions in the peristaltic system. The normal pressure curve created by the peristaltic action of this system is the result of the wave-like motion of pump "fingers" and exhibits no pressure drops as the fluid is pressurized and propelled to the patient. The detection method of the '385 patent appears to require sensing detection of small pressure changes, e.g., as little about 0.6 psi and cannot be applied to situations where the normal pumping cycle exhibits transient pressure drops. Moreover, irrespective of the placement of the sensor, it is commonly not possible to accurately measure this degree of change when detecting across a tube wall. This kind of measurement typically requires insertion of a sensor in the fluid path or operation of a sensor across a flexible membrane adjacent to the fluid path. Both of these options present risks to the sterility of the fluid being infused, a problem that is further complicated where a patient is maintaining his/her own infusion regimen. Sensors in the fluid path would have to be either disposable or re-sterilizeable. Membrane type sensors require a disposable tubing set specific to the sensor.

Downstream occlusions may be detected by a downstream sensor monitoring pressure change in the downstream line. U.S. Pat. No. 4,526,574, for example, discloses measuring an initial tube wall deflection or pressure to determine a fixed baseline value (pre-pumping cycle pressure) at the beginning of the infusion process. Subsequent measurement must be within a predetermined range relative to the fixed baseline value, or an alarm will sound. Additionally, the '574 patent fails to consider the variations that occur in the system over its running time and fails to account for elevated pressure resulting from overfilled medication containers.

Therefore there is a need to develop an improved system and method for detection of up and downstream occlusions. The system and method would operate by pressure detection directly through infusion tubing walls and account for pressure variability resulting from the infusion system, the tubing and the patient. An additional need is the development of an accurate system that avoids compromise of infusion fluid sterility.

SUMMARY OF THE INVENTION

The present invention is directed to a method and a system for monitoring pressure conditions in a fluid pressure upstream or downstream of an intravenous fluid administration pumping system (e.g., an infusion pump) and for detecting upstream or downstream occlusions, respectively. The method and system detect signal changes in fluid pressure across the wall of the tubing so that no interruption in the fluid tubing is required to measure pressure.

For detection of upstream occlusions, the system and method of the invention employ a pressure sensor, a control module and an alarm module. The pressure sensor is positioned upstream of the infusion pump while the control and alarm modules are typically integrated into the pump control modules. During an initial period of operation, the sensor monitors transient pressure conditions which occur during operation including a normal, transient reduced pressure condition produced upstream during un-occluded operation. The control module compares those pressure conditions with user preselected pressure values. If the pressure conditions pass this comparison, the control module stores them as normal operation conditions. The control module then sensed pressure conditions of a currently running pumping cycle with the stored pressure conditions and optionally with the preselected values. The alarm module signals detection of an upstream occlusion and may shut down the pump when the control module determines that a change in the transient, normal reduced pressure condition has occurred.

For detection of downstream occlusions, the system and method of the invention also employ a pressure sensor, a control module and an alarm module. The pressure sensor is positioned downstream of the infusion pump while the control and alarm modules are typically integrated into the pump control modules. During an initial period of operation, the sensor monitors transient and "steady state" pressure conditions which occur during operation including the transient, increased pressure condition produced downstream during un-occluded operation and the "steady state" pressure present after a pumping cycle is completed (hereinafter baseline pressure condition). The control module compares those pressure conditions with user preselected pressure values. If the pressure conditions pass this comparison, the control module stores them as normal operation conditions. The control module then compares sensed pressure conditions of a currently running pumping cycle with the stored pressure conditions and optionally with the preselected values. The alarm module signals a downstream detection of occlusion when the control module determines that a change, preferably an increase, in the transient maximum increased pressure condition has occurred and/or a change in the steady state pressure condition represented by the baseline pressure condition has occurred.

Because the upstream and downstream pressure sensors only need to monitor relative pressure conditions rather than measure absolute pressure, low cost sensors can effectively be used to identify changes in the pressure profile across the tube wall which signify occlusions.

The present invention further preferably incorporates a normalization process into the above-desired method and system. The normalization process accounts for changes in the normal tube force and/or tube resiliency. The process allows for accurate pressure measurements across the tube wall and is based upon measurement of changes in overall tube force over time. Use of the normalization process preferably improves the accuracy of the detection of upstream and/or downstream occlusions. Preferably, the detection can be made with only one pump activation, so that misdelivery can be minimized.

The normalization process is performed by the pressure sensor and control module. The process involves taking a series of tube force measurements at certain times during a pumping cycle and comparing such measurements taken over a series of cycles. To make the measurements, the tubing is uniformly contacted with, and is preferably partially compressed against, the sensor. In an initial measurement step, an estimated tube force is determined, preferably before the first infusion cycle. In subsequent measurement steps for the normalization process, one or more pre-cycle tube force measurements are taken prior to the beginning of each pumping cycle. If the estimated tube force is greater than such cycle force measurements, the estimated tube force is revised as a function of the difference between the estimated tube force and the cycle force measurements. Alternatively the estimated tube force can be decreased by a preset factor as a function of the time period since the initial force measurement. The preset factor is based upon a standard relaxation curve for the tubing involved. The function preferably is a linear function logarithmic of time.

In addition, the present invention preferably includes a further process to account for change of tubing resiliency due to change of temperature. This process is used in conjunction with the normalization process. The process involves adjustment of tubing resiliency as a function of tubing temperature.

When the normalization process is used with occlusion detection, the fluid pressure of concern is determined as a function of the difference between a measured force and the revised estimated tube force. This determination reduces inaccuracy in the pressure readings due to changes in the tubing over time. When the upstream pressure decreases under this normalization process, an occlusion rather than tube relaxation is indicated when a difference is present between the upstream and downstream estimated tube forces, or a difference is present relative to a standard curve for the estimated tube force.

DETAILED DESCRIPTION OF THE PREFERRED EMBODIMENT

The present invention is directed to a method and system for detecting transient signal changes in upstream and/or downstream fluid pressure across a wall of a tubing in an infusion apparatus so as to enable identification of an upstream and/or downstream occlusion. As discussed in greater detail below, the presence of an upstream and/or downstream occlusion is signalled if a respective change in a transient upstream pressure condition or a transient or steady state downstream pressure condition is detected. The signal may be visual, audible, tactible or any combination thereof. The signal may be given at an infusion apparatus site, at a remote location such as a nursing station or a readily observed or felt location on the body of the patient. The present invention further preferably incorporates a normalization process for determining the fluid pressure in a fluid tube across the tube wall where the normal tube force changes over time. This process may be used with the upstream or downstream sensing system and method.

The system and method of the invention may be used with any kind of infusion pumping apparatus. Medical facility systems such as in-patient hospital systems for drugs, blood, fluids and the like as well as home care and ambulatory systems can be adapted to be used with the present invention. Any pumping mechanism will work with the present invention. Included are peristaltic, roller, expulsor, piston/cassette, sequential "finger" and other mechanisms for moving fluid in a tube.

Figure 1:
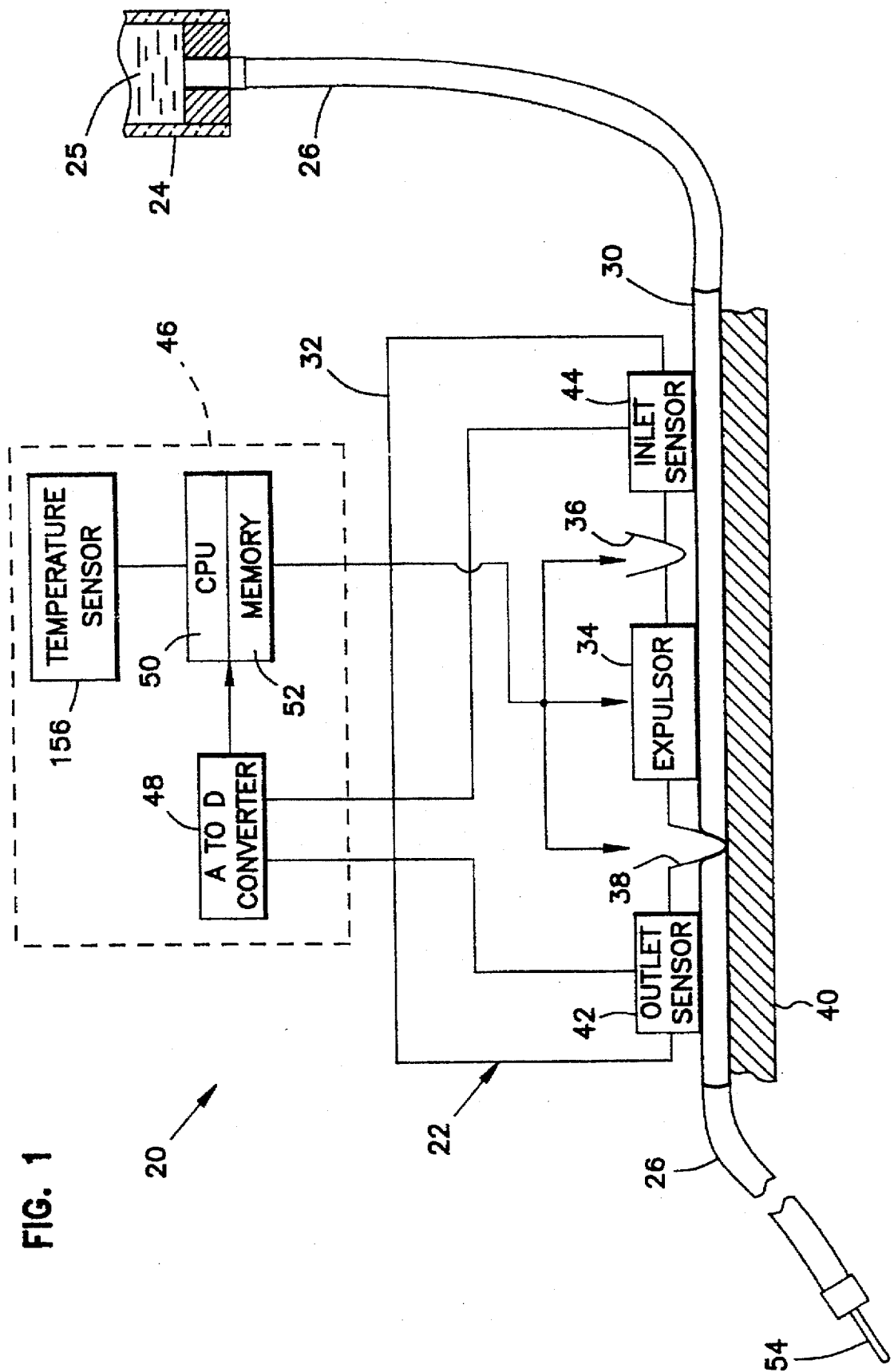
FIG. 1 is a schematic illustration of an exemplary embodiment of an intravenous fluid administration system using an expulsor pump.

FIG. 1 illustrates a schematic diagram of a preferred intravenous fluid administration pumping system 20 using an expulsor infusion pump 22, according to one exemplary embodiment of the present invention. See also U.S. Pat. Nos. 4,565,542; 4,650,469; 5,181,910 and 4,559,038 for examples of further administration pumping systems, the disclosures of which are incorporated herein by reference. According to FIG. 1, a cassette 24 containing a fluid 25 may be connected to a pump segment tubing 30 by a tubing 26. A needle 54 is provided at a downstream end of tubing 26 for administering fluid 25 to a patient. As will be discussed in more detail below, pump segment tubing 30 preferably has a larger diameter and greater resiliency than tubing 26. The larger diameter of tubing 30 allows for more fluid to be pumped for each pump activation and the greater resiliency provides sufficient durability to withstand repeated deformation during pumping.

Figure 2:
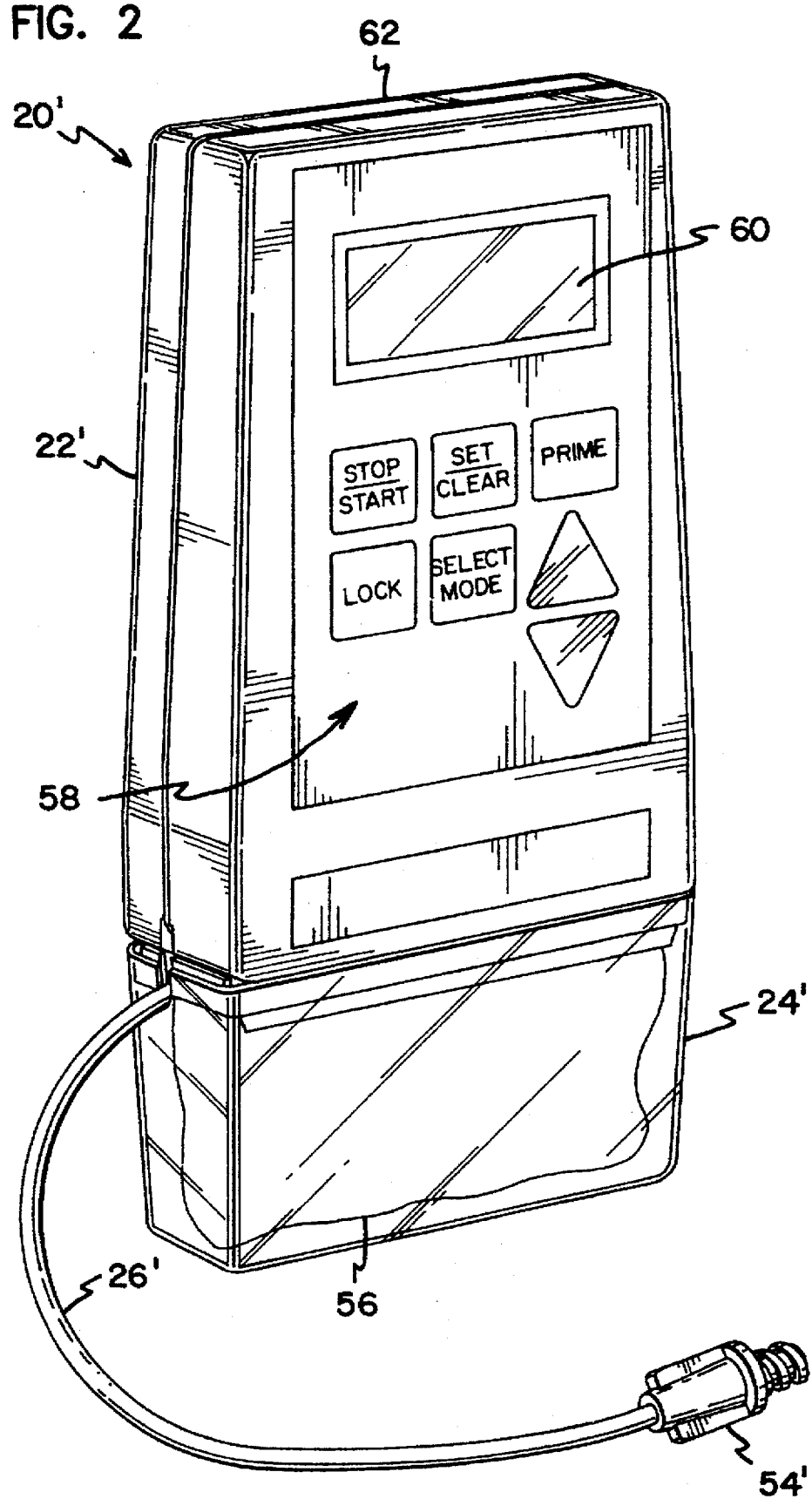
FIG. 2 is a perspective view of a preferred infusion system for use with ambulatory patients.

FIG. 2 illustrates a preferred configuration 20' of the fluid administration pumping system 20 for providing ambulatory infusion that is schematically diagramed in FIG. 1. A container 24' is preferably a cassette or cartridge which is attached to expulsor infusion pump 22' to form a unitary structure. Container 24' includes a sterile bag 56 which is in fluid communication with a pump segment tubing (not shown), tubing 26', and needle 54'. Container 24' may also include a pressure plate (not shown) for retaining tubing 30' against infusion expulsor pump 22'.

Infusion expulsor pump 22' preferably includes a housing 62 containing a keypad 58 for inputting operation parameters and a display 60 for monitoring pump operations. The operation of keypad 58 and display 60 may preferably follow the disclosures of U.S. Pat. No. 5,181,910 and U.S. Pat. Application Ser. No. 08/90,738 filed Jul. 13, 1994 now abandoned, the disclosures of which are hereby incorporated by reference.

Turning now to FIG. 1, pump mechanism 32 includes an expulsor 34, an inlet valve 36, and an outlet valve 38. As will be discussed in connection with FIG. 3, expulsor 34 and valves 36, 38 move from a retracted position to an extended position to deform pump segment tubing 30, thereby causing fluid 25 to be propelled through the tubing to the needle, where it is administered to the patient. Pressure plate 40 preferably retains pump segment tubing 30 against expulsor infusion pump 22. In the preferred embodiment, fluid container 24 is a medication container which also incorporates pressure plate 40.

Pump mechanism 32 shown in FIG. 1 may include an outlet sensor 42 for determining the pressure in tubing 26 downstream from outlet valve 38, and an inlet sensor 44 for determining transient fluid pressure upstream of inlet valve 36. As discussed in detail below, the method for determining the fluid pressure in a fluid tube across the tube wall where the normal tube force changes over time is preferably used in combination with sensors 42 and 44.

It will be understood that a variety of devices may be used as force sensors 42, 44 shown in FIG. 1. Examples include silicon piezoresistive sensors, piezoelectric sensors, diaphragm gauges, bending beam sensors or force sensing resistors (FSR). Silicon piezoresistive sensors are available from Motorola Corporation in Arlington Heights, Ill. or Honeywell Corp. of Minneapolis, Minn. Force sensing resistors resemble a membrane switch which changes resistance inversely with applied force. There are also a variety of bending beam style sensors which can accurately measure force as a function of displacement. The bending beam type sensors preferably use either foil type or silicon strain gauges, optical, capacitive and magnetic (Hall-effect) sensors. Preferred sensors include the bending beam sensors. It will be understood that most of the sensors discussed in the foregoing section measure force, which can be converted by a processor module 50 (FIG. 1) into a fluid pressure value.

The pressure readings from these sensors are transmitted to control module 46. As best shown in FIG. 1, control module 46 is preferably physically attached to pump mechanism 32 of expulsor infusion pump 22. Depending on the type of sensor utilized, control module 46 preferably contains an analog-to-digital converter 48, which is in communication with central processing module 50 and a non-volatile memory device 52. Central processing module 50 also controls operation of pump mechanism 32.

Figure 3:
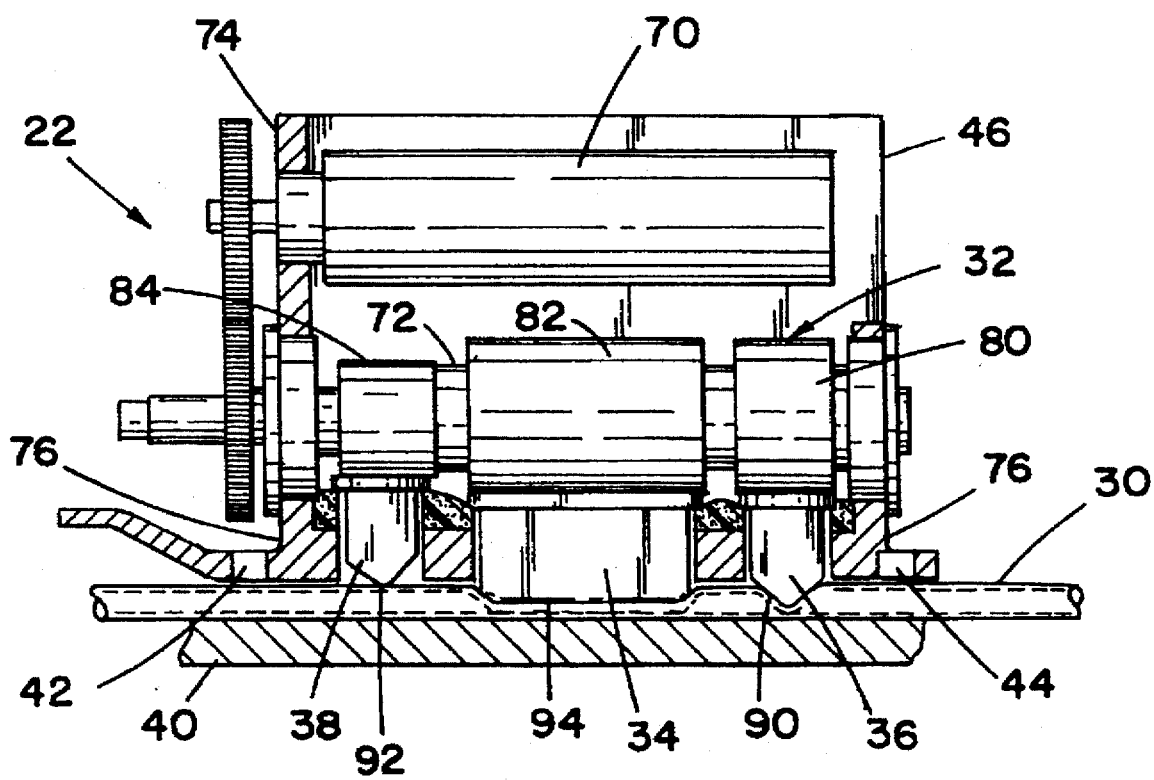
FIG. 3 illustrates a preferred infusion pump according to the invention.

FIG. 3 is a cut-away side view of expulsor infusion pump 22. Because of its small size and weight, pump 22 may be secured to the patient by a belt (not shown), allowing for continuous infusion of the intravenous fluid at the desired rate. However, it will be understood that expulsor infusion pump 22 may be used in a pole-mounted configuration for a non-ambulatory patient, such as shown in U.S. Pat. No. 4,191,184, issued to Carlisle on Mar. 4, 1980, which is hereby incorporated by reference.

Control module 46 of FIG. 3 generally includes a motor 70. A housing (See FIG. 2) is provided to enclose pumping mechanism 32 and control module 46. Expulsor infusion pump 22 includes pressure plate 40, which may be part of a medication container (not shown), as discussed above. Pump segment tubing 30 is positioned between pump mechanism 32 and pressure plate 40.

Pump mechanism 32 includes a rotatable camshaft 72. Camshaft 72 includes a first cam 80, a second cam 82 and a third cam 84. A chassis 74 and braces 76 provide for rotatably holding camshaft 72 to pump mechanism 32.

As discussed above, pump mechanism 32 has inlet valve 36, expulsor 34, and outlet valve 38. Valves 36, 38 and expulsor 34 are reciprocally mounted to chassis 74. Inlet valve 36, expulsor 34, and outlet valve 38 are engageable with respective Cams 80, 82 and 84 such that they are reciprocally removable in response to the rotation of the respective cams. Inlet valve 36 and outlet valve 38 include respective tips 90, 92 for engaging pump segment tube 30 during reciprocal movement. Expulsor 34 includes a surface 94 for engaging pump segment tube 30 during reciprocal movement during the expulsion cycle.

FIGS. 4A through 4E illustrate the sequence of valves 36 and 38 and expulsor 34 movements during an expulsion pumping cycle of preferred pumping system 20 illustrated in FIG. 1. It will be understood that FIGS. 4A-E are not intended to limit the present invention to the expulsor pump discussed above, but are set forth only as an exemplary embodiment. Other pumping mechanisms can be employed as discussed above. It will be further understood that the upstream and downstream sensors can be individually and singly incorporated into the system or incorporated together into the system although the illustration is based upon incorporation together. A graph showing the corresponding pressure measured by inlet and outlet sensors 44 and 42 during each phase of the pumping cycle is provided adjacent to each of the valve configurations shown.

Figure 4A:
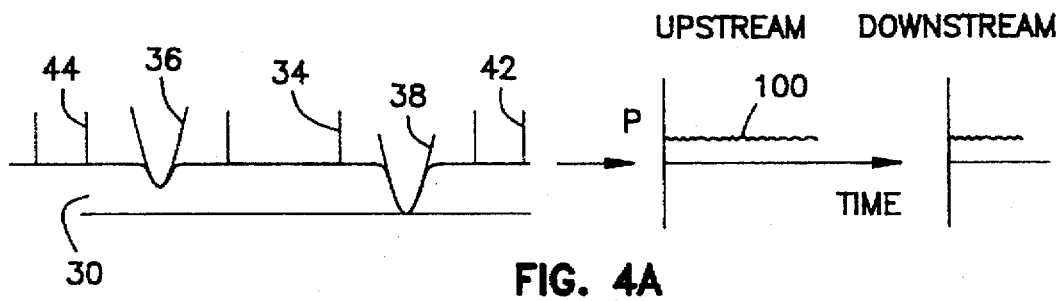
FIGS. 4A through 4E illustrate a preferred sequence of the valves and expulsor mechanism during an expulsor cycle of the exemplary expulsor pump of FIG. 1, with corresponding graphs of the fluid pressure in the tube monitored upstream and downstream of the pump.

FIG. 4A shows outlet valve 38 compressing pump segment tubing 30 to prevent the flow of fluid. Expulsor 34 and inlet valve 36 are in the retracted position and pump segment tubing 30 is fully expanded. Fluid is at equilibrium with the fluid in the medical container (not shown) and the pressure difference resulting from the height of the medication container relative to the pump (upstream head difference). The adjacent pressure-time graphs show the upstream pressure at a relatively stable baseline pressure 100 and the downstream pressure in equilibrium with the patient's fluid pressure.

Figure 4B:
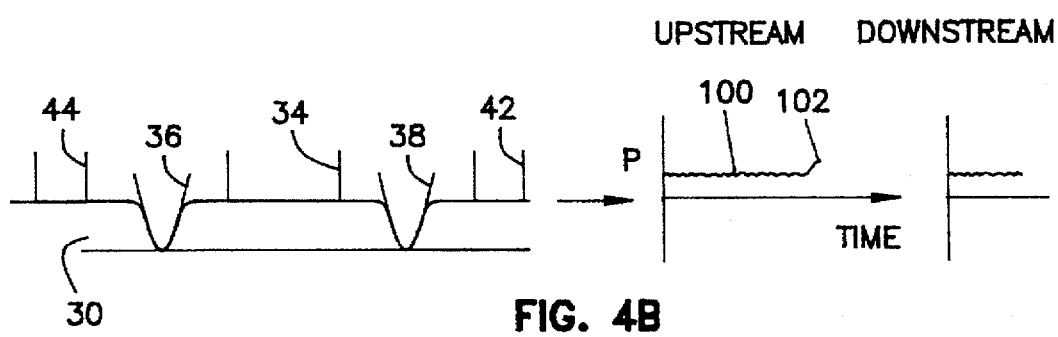

FIG. 4B shows inlet valve 36 extended to compress pump segment tubing 30 closed. Because outlet valve 38 is closed, the extension of inlet valve 36 reduces the volume of the lumen of tube 30, causing a slight pressure increase 102 in the upstream pressure detected by sensor 44. The downstream pressure detected by sensor 42 remains at patient equilibrium and the pressure difference resulting from the height of the pump relative to the patient (downstream head difference).

Figure 4C:
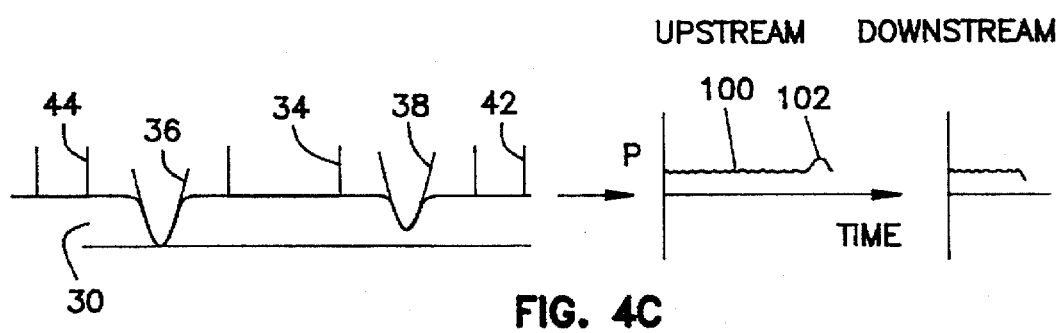

FIG. 4C illustrates outlet valve 38 beginning to move to the retracted position. The movement of outlet valve 38 is isolated from sensor 44 by inlet valve 36 so that there is no impact on sensor 44. The pressure increase 102 caused by the extension of inlet valve 36 dissipates back toward baseline level 100. The transient pressure downstream detected by sensor 42 decreases slightly due to the increased tube volume under outlet valve 38.

Figure 4D:
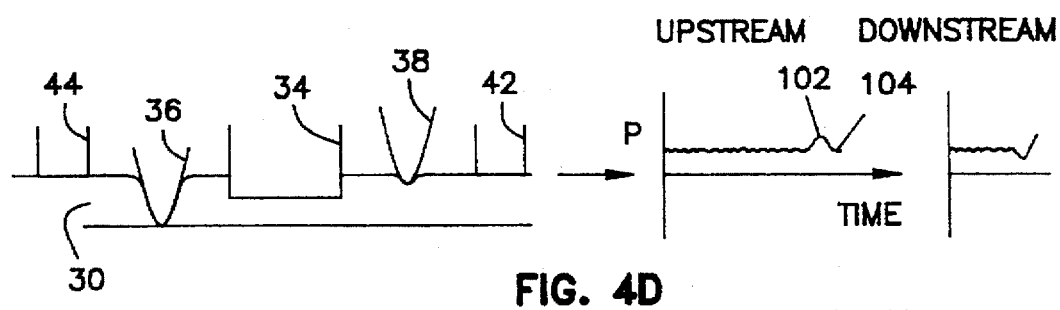

FIG. 4D shows outlet valve 38 in a fully retracted position and expulsor 34 moving to an extended position to compress pump segment tubing 30. The pressure-time graphs for FIG. 4D show a leveling of the upstream pressure to a baseline level 104 and the downstream pressure beginning to increase toward its transient maximum. As expulsor 34 moves to its fully extended position, the fluid in pump segment tubing 30 is expelled into the delivery tubing connected to the patient. Downstream sensor 42 correspondingly detects a transient maximum in pressure which decreases as the fluid is transmitted into the patient (acting as a fluid pump).

Figure 4E:
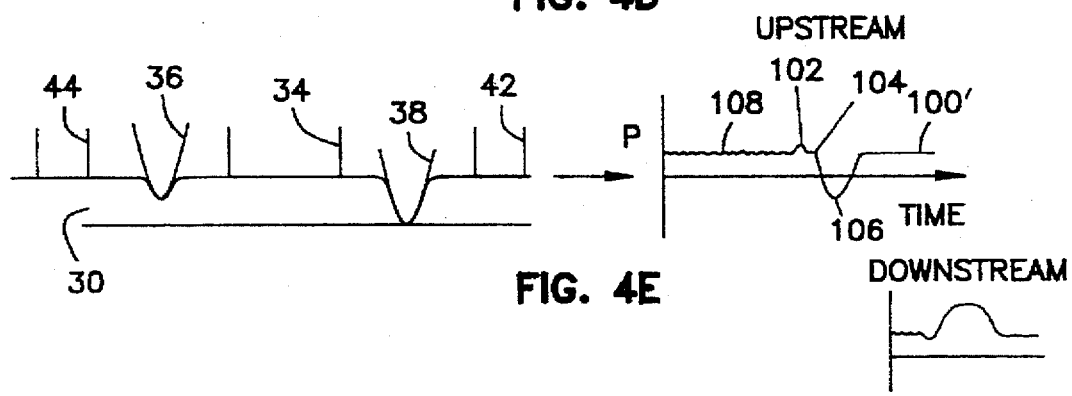

FIG. 4E shows outlet valve 38 again in the extended position and inlet valve 36 and expulsor 34 retracting, in a configuration similar to that shown in FIG. 4A. As pump segment tubing 30 expands, a vacuum is created which draws in fluid from the medication container (not shown). The resilience and elasticity of pump segment tubing 30 causes it to assume its original shape. The expansion of pump segment tubing 30 proximate inlet valve 36 increases the volume available for the fluid, causing a reduced pressure condition to be detected by inlet sensor 44, illustrated as a transient negative spike 106. Generally, the magnitude of negative spike 106 is a function of the amount of fluid displaced by inlet valve 36 and expulsor 34 and the flow impedance of the tubing 26 upstream of expulsor infusion pump 22. After a brief time, the pressure of the fluid in pump segment tubing 30 reaches an equilibrium 100' with the fluid in the medication container (See FIG. 4A). The pressure condition detected by outlet sensor 42 is a baseline equilibrium for the patient's pressure plus any downstream head difference.

Generally, the upstream and downstream pressure conditions represented by graphs 4A through 4E represent the normal operating condition of the system in an un-occluded condition. These pressure conditions are stored in the system memory (e.g. memory device 52, FIG. 1) for use in the pressure comparison method of the invention. Generally, these conditions are present during the initial period, preferably the first few minutes, more preferably the first 2-5 minutes of operation of the system. These initial operating conditions typically are monitored by the trained patient or by a health care medical person such that occlusion would otherwise be noted. The system preferably may include a selected set of pressure conditions preloaded into the system memory. This pre-selected set can be established during manufacture or by the user (e.g., doctor) and represents a set of typical known operating conditions for the system. Preferably included within this pre-selected set are: the operating pressure maximum, the transitory pressure drop at the beginning of the cycle and the transitory safety pressure maximum. Other conditions such as rate of pressure decrease and/or increase during the pumping cycle can also optionally be included. The initial period of system operation preferably can be compared to the pre-selected set to further establish the absence of occlusions during the first few minutes of operation. The comparison is preferably made according to a set of pressure condition deviation parameters installed at manufacture or by the user. The deviation parameters provide for acceptable deviation of the system operation conditions from the pre-selected set conditions. As long as the system is operating within the established deviation parameters for the pre-selected set of conditions, the system accepts and stores the pressure conditions of the initial period of operation as the normal operating conditions. If the system does not accept these conditions, the system preferably shuts down the infusion administration pumping system or otherwise signals that a problem exists.

Generally, occlusions upstream or downstream of the infusion pump are detected by the system of the invention according to a comparison method of the invention. Points on the transient pressure curve detected by the respective sensor are compared with the corresponding points on the normal pressure curve for upstream or downstream pressure which has been stored in the system memory as described above. The general capability for occlusion detection is provided by comparison of the pressure sensed during the present cycle with the stored normal pressure curve according to pump cycle timing. An allowed deviation between the cycle pressure detected and the corresponding point along the normal pressure curve can be included to account for minor transient and/or system variations which occur during normal operation of an infusion pump system.

Figure 5:
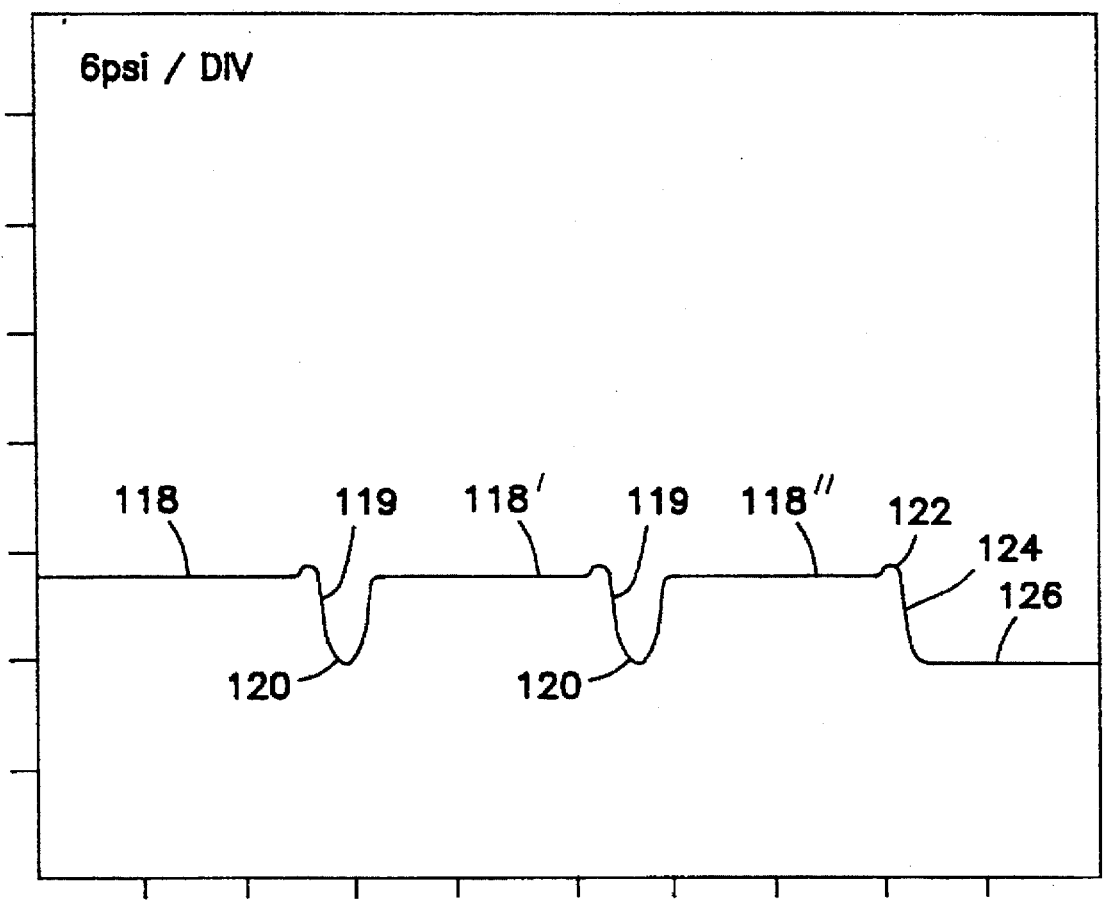
FIG. 5 is a pressure-time graph illustrating an upstream pressure-wave form as the preferred exemplary expulsor pump transitions from normal operation to an upstream occlusion close to the pump.

FIG. 5 is a pressure-time graph measured by the inlet sensor illustrating the transition of the pressure profile from normal operation to an upstream occlusion condition. As discussed in connection with FIGS. 4A and 4E, retraction of the inlet valve causes a negative pressure spike 119 and the pressure drops from a baseline pressure 118 to a reduced pressure condition 120. After the inlet valve has retracted, the pressure generally returns to a pre-activation baseline level 118' and 118".

At a time sequence 122 an upstream occlusion occurs close to the expulsor infusion pump (e.g., within 6 inches). As the inlet valve retracts, the pressure drops below baseline level of 118" causing a negative pressure spike 124. However, because the upstream occlusion prevents the fluid from backfilling the expanded pump segment tubing a reduced pressure condition 126 remains.

Figure 6:
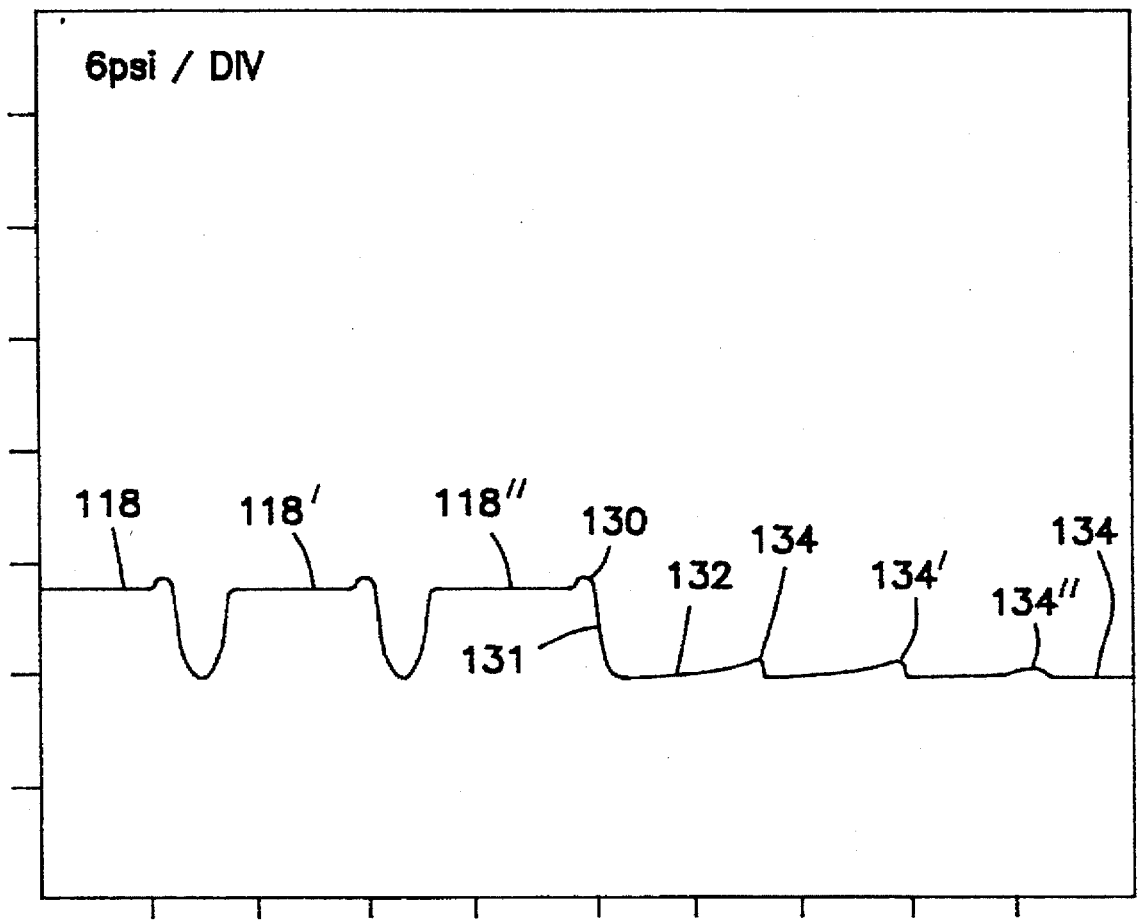
FIG. 6 is a pressure-time graph illustrating an upstream pressure-wave form as the preferred exemplary expulsor pump transitions from normal operation to an upstream occlusion far from the pump.

FIG. 6 illustrates a pressure-time graph for the transition from normal operation to an upstream occlusion far from the pump. FIG. 6 illustrates an upstream occlusion approximately 60 inches from the expulsor infusion pump. Up until time sequence 130 where the occlusion occurs, the pressure-time graph appears substantially the same as in FIG. 5. Retraction of the inlet valve causes a negative spike 131 (FIG. 6). However, the occlusion prevents a reduced pressure condition 132 from returning to a baseline level (e.g., 118, 118', 118"). The reduced pressure condition 132 causes the resilient tubing to collapse, allowing a slight pressure increase 134 to be detected by the inlet sensor. With each subsequent expulsion cycle, a pressure increase 134', 134" becomes smaller, until the upstream tubing is effectively collapsed and a stable, reduced pressure condition 126' is reached.

Figure 7:
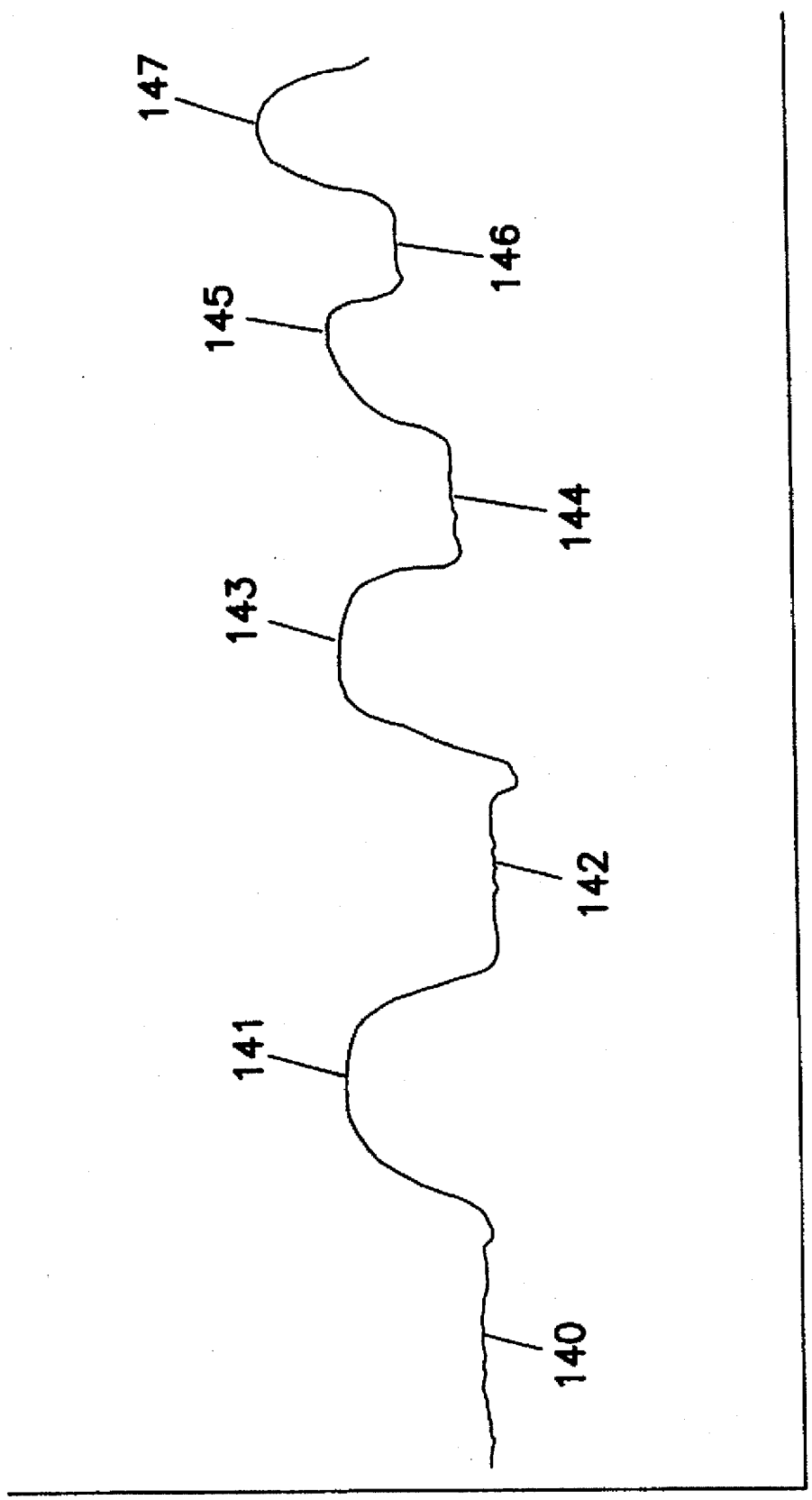
FIG. 7 is a pressure-time graph illustrating a downstream pressure-wave form as the preferred exemplary expulsor pump transitions from a normal operation to a downstream occlusion between the pump and the patient.

FIG. 7 illustrates a pressure-time graph for the transition from normal operation to a downstream occlusion between the expulsor infusion pump and the patient. Until time sequence 130' where the occlusion occurs, the pressure-time graph appears substantially the same as the sequences shown in the downstream pressure-time graphs for FIGS. 4A through 4D. Retraction of the outlet valve and extension of the expulsor compress the pump segment tubing and expel the fluid in that pump segment tubing into the delivery tubing connected to the patient. However, the occlusion prevents the fluid from passing into the patient. The larger than normal volume of fluid in the delivery tube causes the transient maximum pressure condition measured by the outlet sensor to increase above a normal maximum pressure condition. In addition, the increased volume prevents the pressure maximum from decreasing to a normal baseline or steady state condition. Instead, the larger than normal volume of fluid in the delivery tube establishes a higher baseline or steady state downstream pressure condition. With each subsequent expulsion cycle, the steady state pressure downstream in the patient delivery tube is step-wise increased until the downstream steady state pressure theoretically equals the maximum pressure capability of the pump. Long before this condition is reached, however, the maximum pressure changes and the step-wise steady state signal changes detected by the downstream sensor across the wall of the tubing will identify a downstream occlusion.

Generally, if pressure drops as shown by points 124 and 126 of the graph FIG. 5, or points 131 and 132 of the graph FIG. 6, appear through the comparison process, an upstream occlusion is indicated. Preferably, the system notes the pressure drop and the absence of a pressure rebound to the original baseline value or a continuation of a decreased steady state condition of the baseline. The system will immediately signal that an upstream is pressure is present when this condition occurs. Likewise, as shown by points 142, 144, 146 of graph FIG. 7, if a step-wise increase in the baseline or steady state pressure condition downstream relative to the corresponding pressure of a normal pressure curve in the system memory occurs or a significantly higher pressure maximum relative to the corresponding pressure of the normal pressure curve occurs (points 143, 146), a downstream occlusion is indicated. The system will immediately signal the presence of a downstream occlusion when either of these conditions occurs. The allowed deviation gap or magnitude for the pressure difference required for signalling the presence of an upstream or downstream occlusion can be adjusted from a minimum of 2 psi up to 30 psi. The allowed deviation gap also can be adjusted according to the type of tubing composition present, the tubing size, and other fixed properties of the tubing.

According to the system and method of the invention, the tube force/tube resiliency normalization process is also preferably incorporated into the method for pressure condition determination. Infusion tubing has a tendency to "stress relax" over time due to its polymeric nature, affecting the accuracy of pressure readings by the sensor. Furthermore, the pressure readings provided by the sensor through the tubing wall include not only the fluid pressure component but also the pressure or force of the wall itself. Therefore, the system preferably incorporates a process to account for these factors so as to increase the accuracy of pressure measurement.

The process generally involves partially compressing the tubing against the sensor so that the resilience of the tubing exerts a measurable force. This measurement is made with fluid in the tubing but before the fluid is pressurized. It provides an "estimated tube force" value. The "estimated tube force" can then be subtracted from a tube wall force measurement after the fluid is pressurized in order to determine the actual fluid pressure. However, as the tubing relaxes, the tube force will decrease, causing potential inaccuracy in the fluid pressure measurement. Consequently, a relaxation factor is factored into the tube force normalization process. The determination of that relaxation is discussed in detail below.

The relaxation factor maybe independently determined and maintained for upstream and downstream tubing. The reason is that upstream and downstream tubing relaxation may differ due to differences in the tubing or due to differences in the intial stress.

While the following discussion generally reflects using the outlet sensor to evaluate tube relaxation upstream and downstream, it will be understood that either of inlet and sensors 42, 44 or both may also be used for establishing the normalization process and preferably the inlet and outlet sensors are used together for independent normalization upstream and downstream. All structural features mentioned in the following discussion are based upon FIG. 1.

Figure 8A:
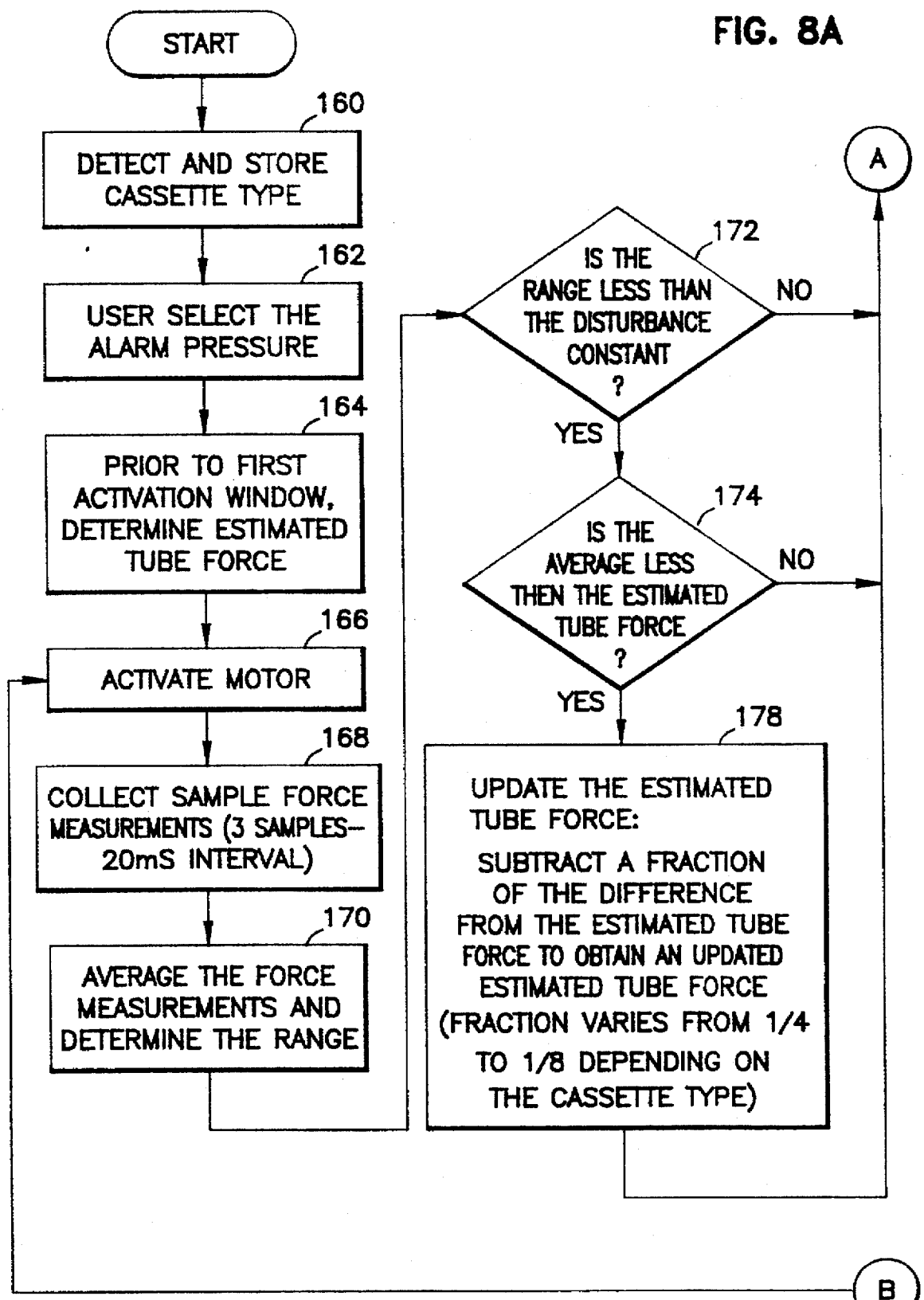
FIGS. 8A and 8B are flow charts showing a preferred process, method and system for determining the fluid pressure in a fluid tube across the tube wall of the preferred expulsor pump and system where the normal tube force changes over time and for detecting transient signal changes in an upstream or downstream detector across the wall of the tubing to identify upstream or downstream occlusions.
Figure 8B:
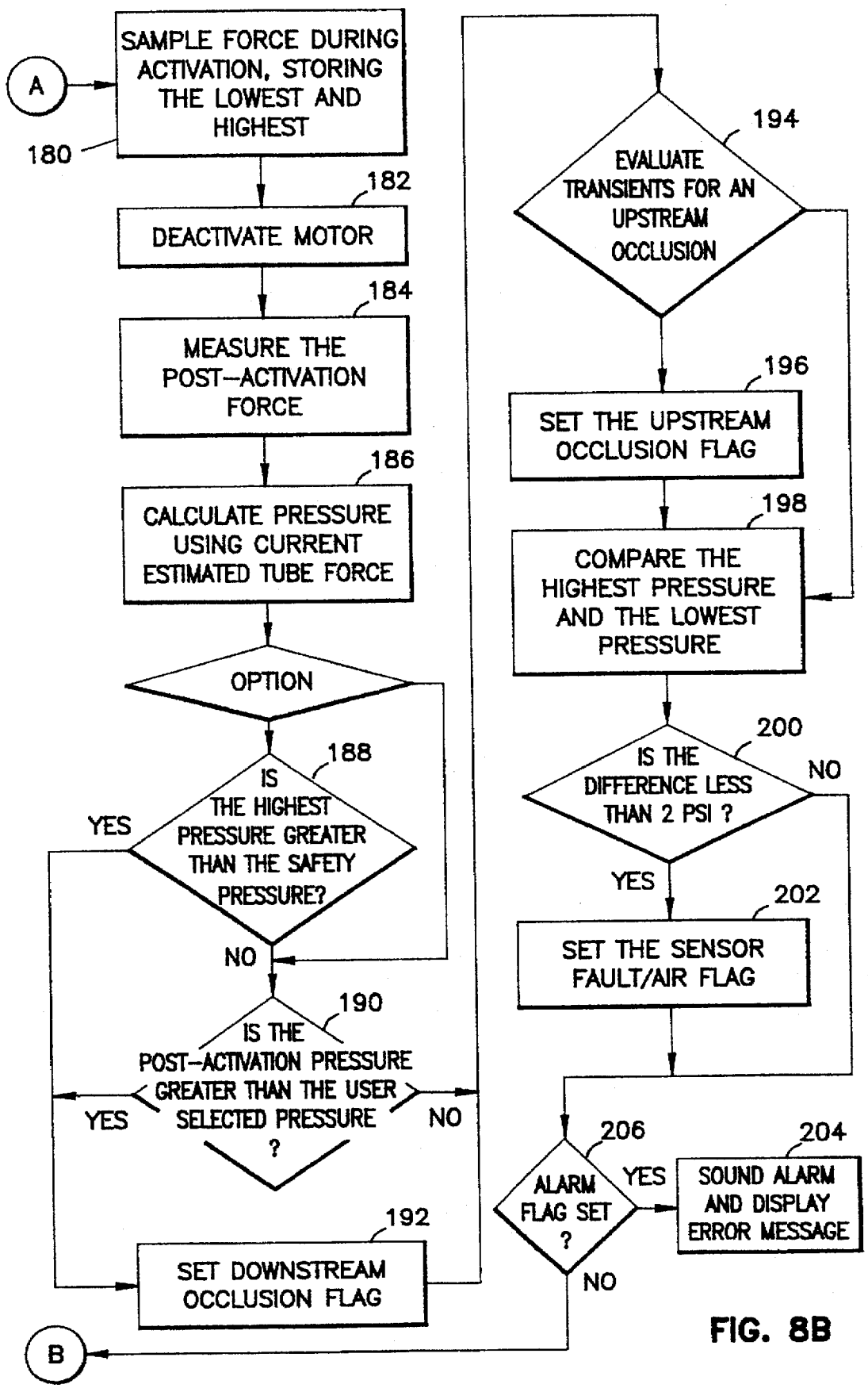

The details of the process of the invention to normalize force or pressure readings due to tube force variations such as stress relaxation are shown by FIGS. 8A and 8B as flow charts of the process steps. The flow charts show how to determine the fluid pressure in a fluid tube across the tube wall where the normal tube force changes over time. It also shows how to detect transient signal changes detected by upstream and/or downstream sensors across the wall of the tubing and identify upstream and/or downstream occlusions, respectively. The software for conducting this process is preferably stored in a non-volatile memory device 52 (FIG. 1) and executed in CPU 50 (FIG. 1).

As shown in FIG. 8A, preliminary steps taken before conducting the steps for tube force factoring include establishment of working parameters for the system. The process takes input information about the type of medication container being used, step 160, and the user selected pressure values (e.g., maximum alarm pressure, step 162) for infusion operation. The first preliminary step involves conformation of the medication container. The control module of expulsor fusion pump preferably detects and stores, at step 160, the type of medication container attached to the expulsor pump. Alternatively, the type of medication container may be input by the user using a keypad or some other input device (See FIG. 2).

In a second preliminary step, the system preferably provides the user with the option to pre-select pressure values such as the normal baseline, transient pressure decrease, operating maximum and safety maximum pressures discussed above. Preferably at least the value corresponding to the maximum operating pressure for the system, as measured by the outlet sensor is set. Alternatively, the alarm pressure may be preset by the health care provider or the pump manufacturer. The user alarm pressure limit 162 is preferably a function of the flow impedance of the system. Where the flow impedance is large, a larger user selected alarm pressure is preferred in order to prevent false occlusion alarms. On the other hand, where the flow impedance of the system is low, a lower user selected alarm pressure will provide greater sensitivity to occlusions.

After completion of the preliminary steps, the process for factoring of tube force variations is begun. According to this process, an estimated tube force measurement, step 164, is preferably taken by the outlet sensor before the fluid is pressurized by the pump, e.g., before the first infusion cycle. This estimated tube force generally equals the force necessary to compress the tube in the area of the pressure sensor, as a result of the stiffness or resiliency of the tube, assuming there is no pressure differential across the wall of the tube due to atmospheric pressure. This determination is made according to the partial compression technique discussed above. Since there is generally a time delay between pump activations, any pressure build-up in the tube during un-occluded infusion normally dissipates before the next activation, so that there is no pressure differential across the tube wall.

As diagrammed in FIG. 8A (structural features reference FIG. 1), pump segment tube 30 is preferably partially compressed between sensor 42 and pressure plate 40 so that sensor 42 will register a tube force (estimated tube force) when fluid 25 is not pressurized by the pump. The estimated tube force may be subtracted from the force measurements obtained after the pump is activated to determine the actual fluid pressure. However, as is discussed below, the estimated tube force is evaluated prior to each infusion cycle and updated to compensate for changes in tubing 26 over time.

Pump motor 70 is then activated at step 166 (FIG. 8A). Immediately after motor 70 is activated at step 166, a group of one or more sample force measurements 168 are taken by the sensor. The sample force measurements 168 are taken immediately prior to the infusion cycle. Because of the arrangement of cams 84 in the preferred exemplary embodiment, there is approximately a short delay (about 100 ms) between the time when motor 70 is activated and when outlet valve 38 begins to open. Consequently, sample force measurements 168 are taken before fluid is pumped by system 20. With regard to inlet sensor 44, a pressure reading is preferably taken prior to the retraction of inlet valve 36.

Because the upstream pressure also drops when there is an upstream occlusion, the normalization process also determines whether the upstream pressure decrease is due to tube relaxation or an occlusion. This determination is accomplished either by comparing the estimated tube forces measured upstream and downstream, or by comparing the upstream sensed pressure with a standard relaxation curve. A significant deviation (at least about ±2 psi) in either of these comparisons means that an upstream occlusion is also causing at least part of the pressure drop.

The microprocessor 50 (FIG. 1) then determines an average and a range (maximum and minimum readings) 170 (FIG. 8A) after motor activation but before the pumping cycle begins. If during the first pump activation the range is larger than a disturbance constant 172, average 170 is discarded and estimated tube force 164 or 178 is used in its place. Disturbance constant 172 is a measure of pressure variability and is a pre-set, selected value inputted by the manufacturer or user (e.g., doctor). This constant allows determination whether the force prior to the expulsion cycle is sufficiently stabilized to determine a baseline value.

The estimated tube force is updated by subtracting a fraction of the difference between the average of force measurements 170 and the estimated tube force. If this new intermediate value is less than the estimated tube force, the estimated tube force is replaced by the new intermediate value.

Preferably, the estimated tube force is updated only by some percentage of that difference. In this way, updated estimated tube force 178 stored by the system is similar to a running average which tends to lag behind the actual force measurements being measured. This lag is desireable in order to prevent an anomalous pressure reading from dramatically altering the estimated tube force, and subsequently causing an erroneous evaluation of the pressure profile of system 20. If average 170 is greater than estimated tube force 164, adjustment 178 is not made to estimated tube force 164.

As shown in FIG. 8B, sample force readings are taken during a fluid pumping cycle 180, and the lowest and highest values are stored for future use. After motor 70 is deactivated at step 182, a post activation force is measured 184. Updated estimated tube force 178 is then subtracted from post activation force 184 and the minimum and the maximum force measured at cycle 180. These values are used to calculate the maximum pressure rise and the post activation pressure.

As indicated above, there may be a manufacturer determined maximum operating pressure for system 20. This maximum pressure may generally correspond to a pressure somewhat below (e.g., 5 to 10 psi) the pressure needed to compromise the weakest part of the fluid line and associated components of system 20. If at any time during pumping cycle 180, that maximum operating pressure is exceeded (as measured by outlet sensor 42) system 20 preferably terminates operation and a downstream occlusion is signalled at step 188 (FIG. 8B). If the highest pressure reading during pumping cycle 180 is less than the maximum operating pressure of system 20 according to step 188 (FIG. 8B), microprocessor 50 may then evaluate at step 190 (FIG. 8B) whether the post-activation pressure is greater than a user-selected downstream pressure limit 162. Alternatively or additionally, if the post-activation pressure exceeds user-selected downstream pressure limit 162, a downstream occlusion is signaled 192 (FIG. 8B).

In a system which includes upstream and downstream sensors, if the post-activation pressure does not exceed the user-selected downstream pressure limit at step 190, the system then evaluates whether an upstream occlusion has occurred. The upstream occlusion pressure limit is preferably preset by the manufacturer of the pump but may alternatively be selected by the user.

Upstream occlusions are detected at step 194 (FIG. 8B) by evaluating the transient pressure readings at upstream sensor 44 using a variety of possible techniques. For example, it is possible to measure the magnitude of the negative spike 124 (FIG. 5) and compare it with the normal negative spikes 119 (FIG. 5).

Alternatively, the magnitude of the distance between reduced pressure condition 126 (FIG. 5) and baseline level 118 (FIG. 5) can provide an indication to be monitored and an occlusion indicated if the magnitude exceeds a predetermined value.

Alternatively, measure the change in pressure, from atmospheric to some negative value, using the moving estimated tube force to determine the baseline or atmospheric (and head height) value.

Another alternative for pressure condition comparison involves monitoring the magnitude of the change in pressure over time. This variable corresponds to the slope of the pressure-time graph. If the slope of the negative spike exceeds a certain value, an occlusion is indicated.

The occurrence of a positive change in pressure over time after the occurrence of a negative change in pressure over time can also be used to identify upstream occlusion. The absence of a positive slope after the occurrence of a negative scope would indicate an upstream occlusion.

Finally, system 20 determines if pump 32 is attempting to pump air by comparing the highest pressure and lowest pressure values during an expulsion cycle 198. For example, if the difference is less than approximately 2 psi at step 200, the system indicates that only air is being pumped or that the sensor has failed.

The user is notified that an occlusion has occurred preferably by an audible alarm and an error message on an operating display 204. If no error has occurred, motor 70 is activated 166 for another expulsion cycle.

Figure 9:
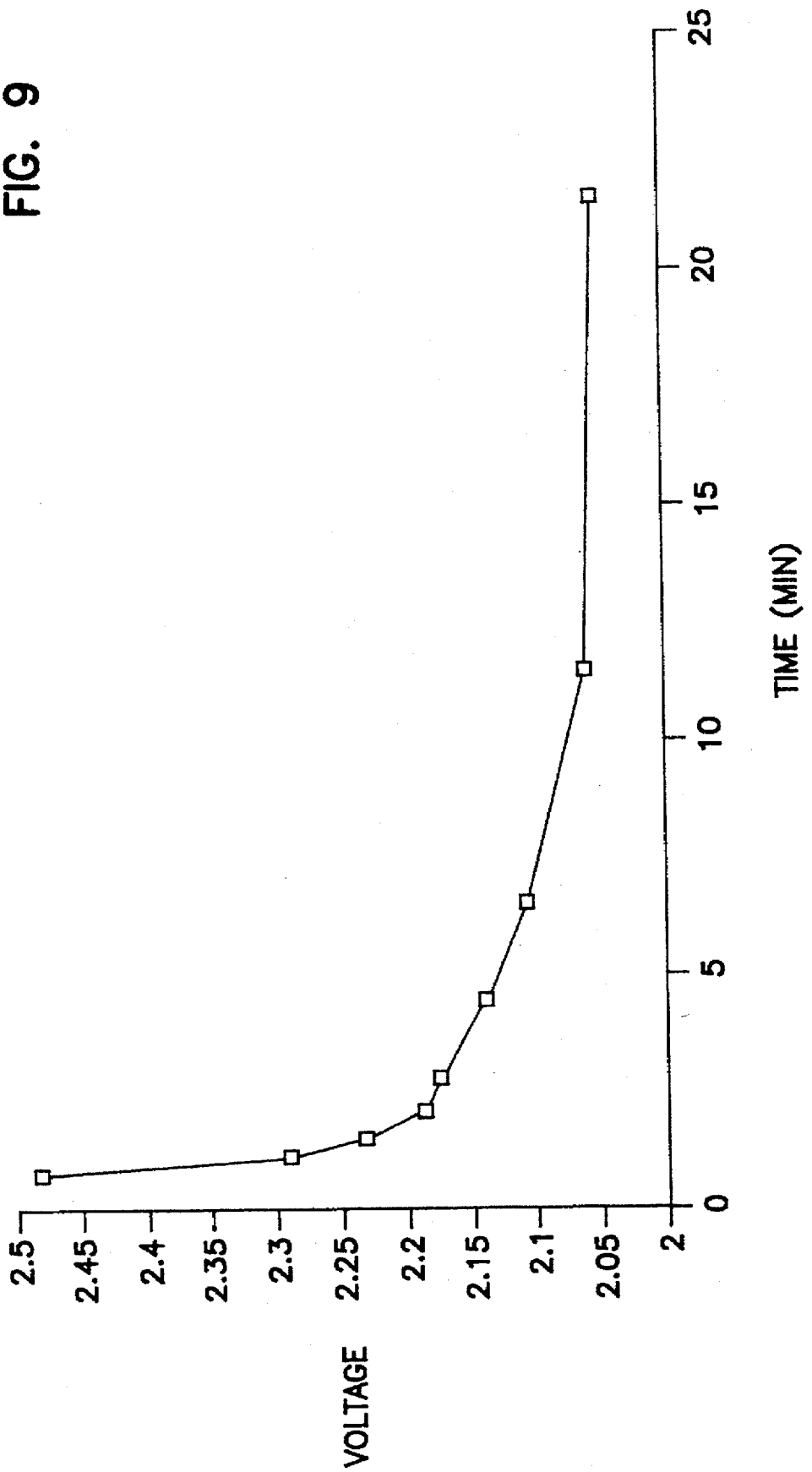
FIG. 9 is a graph illustrating a sample of the change in voltage produced by the sensor and indicating tube force relative to time.

An advantage of the present invention is its accounting for changes in tube force factors during operation of the infusion system. These changes can be significant and can greatly affect pressure determination made by the system. FIG. 9 is an exemplary graphical illustration of the estimated tube force reading (voltage) detected over time and illustrates the benefits of the above-mentioned advantage of the invention. The graph shows how stress relaxation can change the force necessary to compress the tube over time. The graph was obtained by direct force measurement of the tubing over time by the sensor.

In addition to the stress relaxation effects upon fluid pressure, temperature can affect tube force and sensor function. Because the tubing is elastomeric, it is softer at higher temperatures. Another advantage of the invention provides for an accounting of pressure variations due to temperature. For example, controller 46, which has an internal clock, can be programmed to electronically compensate for these increases in the voltage reading for a given pressure over a range of temperatures. Therefore, fluid pressure may be evaluated as function of force, temperature, and time: Pressure=f(Force, Temp., time).

Figure 10:
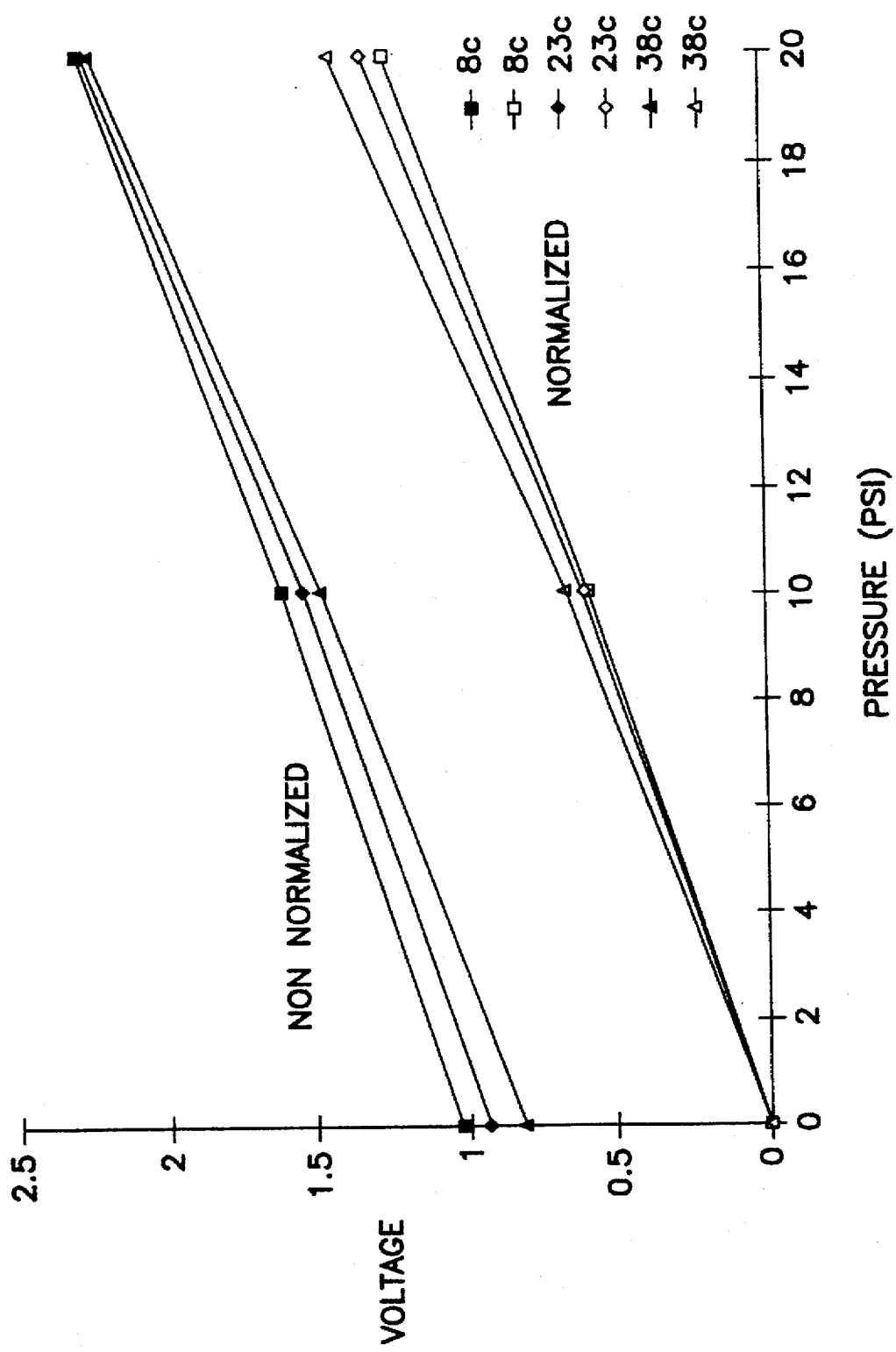
FIG. 10 presents curves of the voltage readings at various pressure levels for the tubing at 8° C., 23° C., and 38° C.

FIG. 10 illustrates the benefits of accounting for the effect of temperature upon fluid and tube pressure. This figure depicts a series of examples of the voltage generated by the sensors 42, 44 as a function of pressure for 8° C., 23° C. and 38° C. Each curve in the top grouping of curves corresponds to the non-normalized tube force measured as a voltage for each medication container evaluated (one for each normalized and non-normalized temperature). The bottom grouping of curves corresponds to the top grouping with the initial tube force subtracted out (i.e., normalized). The bottom grouping which excludes tube force, illustrates the variable effect of temperature upon the signal generated by the fluid pressure. If there were no variation, one line should appear. As is well known, however, temperature inversely affects tubing resiliency. As the temperature increases, the tubing resiliency decreases and the corresponding measured voltage increases as shown by the difference in scopes for the bottom grouping of curves. A temperature sensor 156 may be included with the control module in order to provide more accurate pressure readings during operation of the infusion pump.

Other modifications of the invention will be apparent to those skilled in the art in view of the foregoing descriptions. These descriptions are intended to provide specific examples of embodiments which clearly disclose the present invention. Accordingly, the invention is not limited to the described embodiments or to the use of specific elements, dimensions, materials or configurations contained therein. All alternative modifications and variations of the present invention which fall within the spirit and broad scope of the appended claims are covered.

What is claimed is:

1. An occlusion detection system comprising:
 a fluid tube;
 an infusion pump, the fluid tube operatively engaged to the infusion pump, the infusion pump having an inlet valve, an expulsor valve and an outlet valve, the valves engaging the tube to force fluid through the tube at a baseline pressure, the valves further operative to create a normal negatively directed transient pressure condition less than the baseline pressure upstream of the pump during un-occluded operation:
 a pressure sensor connected to the fluid tube of the infusion pump for monitoring the negatively directed transient pressure;
 a control module connected to the sensor, the control module including means for detecting an absence of the negatively directed transient pressure in fluid tube; and
 an alarm module for signaling an upstream occlusion when the means for detecting indicates the negatively directed transient pressure condition is absent.

2. The system according to claim 1, wherein the pressure sensor is a force sensing resistor, a piezoresistive sensor, a piezoelectric sensor, a diaphragm piston gauge, a bending beam gauge, a strain gauge or a hall-effect sensor.

3. A system as in claim 1 further comprising a second pressure sensor operatively connected to the fluid tube downstream of the infusion pump for monitoring the pressure in the fluid tube downstream of the infusion pump, the control module further connected to the second pressure sensor, and further configured to compare the pressure in the fluid downstream of the infusion pump against a predetermined threshold, and the alarm module further configured to signal a downstream occlusion when the control module indicates that the downstream fluid pressure exceeds the threshold.

4. A system according to claim 3, which includes a third control circuit for determining priority between the downstream and upstream detector control circuits.

5. The system according to claim 3, wherein the pressure sensor is a force sensing resistor, a piezoresistive sensor, a piezoelectric sensor, a diaphragm piston gauge, a bending beam gauge, a strain gauge or a hall-effect sensor.

6. A system according to claim 3, wherein the infusion pump is selected from the group consisting of a peristaltic pump, a roller pump, an expulsor pump, a finger pump and a piston cassette pump.

7. A system according to claim 3, wherein the infusion pump is selected from the group consisting of a peristaltic pump, a roller pump, an expulsor pump, a finger pump and a piston cassette pump.

8. A system for determining the fluid pressure in a fluid tube of an infusion system where the fluid tube is partially compressed by a pressure sensor and the fluid tube exerts a tube force on the sensor that changes over time, the infusion system having a first and subsequent infusion cycles, comprising:
 a control module connected to the sensor for receiving force readings, for calculating fluid pressure, and for controlling the infusion cycle;
 first means for determining an estimated tube force on the sensor due to the stiffness of the tube prior to the first infusion cycle;
 means for acquiring a tube force measurement prior to an infusion cycle;
 second means for determining if the force measurement prior to an infusion cycle is less than the estimated tube force including means for updating the estimated tube force if the force measurement is less than the estimated tube force as a function of the difference between the estimated tube force and the force measurement; and
 means for calculating and storing the fluid pressure as a function of at least the force measurement less the estimated tube force.

9. A system according to claim 8, wherein the second means for determining employs a standard relaxation curve for the tubing to update the estimated tube force.

10. A system according to claim 8, which further comprises a system for detecting an upstream occlusion comprising:

a pressure sensor operatively connected to the fluid tube upstream of the infusion pump for monitoring the transient pressure changes in the fluid tube upstream of the infusion pump during an infusion cycle, a control module connected to the upstream sensor, the control module including means for identifying transient pressure conditions during un-occluded operation and means for comparing a reduction in fluid tube pressure during an infusion cycle with the pressure conditions identified during non-occluded operation; and an alarm module for signaling an upstream occlusion when the means for comparing indicates the reduction in pressure does not compare with the transient pressure conditions identified during un-occluded operation.

11. A system according to claim 8, which further comprises a system for detecting a downstream occlusion comprising:

a pressure sensor operatively connected to the fluid tube downstream of the infusion pump for monitoring the transient pressure changes in the fluid tube downstream of the infusion pump during an infusion cycle, a control module connected to the downstream sensor, the control module including means for identifying the transient pressure maximum condition and baseline steady state during un-occluded operation and means for comparing the transient pressure maximum and baseline steady state during an infusion cycle to the pressure conditions identified during un-occluded operation, and an alarm module for signaling a downstream occlusion when the means for comparing indicates the transient maximum or baseline steady state pressure change does not compare with the pressure conditions identified during un-occluded operation.

12. A system according to claim 8, which further comprises a system for detecting upstream and downstream occlusions comprising:

an upstream pressure sensor operatively connected to the fluid tube upstream of the infusion pump for monitoring the transient pressure changes in the fluid tube upstream of the infusion pump during an infusion cycle, a control module connected to the upstream sensor, the control module including means for identifying transient pressure conditions during un-occluded operation and means for comparing a reduction in fluid tube pressure during an infusion cycle with the pressure conditions identified during non-occluded operation;

an alarm module for signaling an upstream occlusion when the means for comparing indicates the reduction in pressure does not compare with the transient pressure conditions identified during un-occluded operation;

a downstream pressure sensor operatively connected to the fluid tube downstream of the infusion pump for monitoring the transient pressure changes in the fluid tube downstream of the infusion pump during an infusion cycle, a control module connected to the downstream sensor, the control module including means for identifying the transient pressure maximum condition and baseline steady state during un-occluded operation and means for comparing the transient pressure maximum and baseline steady state during an infusion cycle to the pressure conditions identified during un-occluded operation, and an alarm module for signaling a downstream occlusion when the means for comparing indicates the maximum or baseline steady state pressure change does not compare with the pressure conditions identified during un-occluded operation.

13. An occlusion detection system comprising:

a fluid tube;

an infusion pump, the fluid tube operatively engaged to the infusion pump, the infusion pump having an inlet valve, an expulsor valve and an outlet valve, the valves engaging the tube to force fluid through the tube at a baseline pressure, the valves further operative to create a normal negatively directed transient pressure condition less than the baseline pressure upstream of the pump during un-occluded operation;

an upstream pressure sensor connected to the fluid tube upstream from the infusion pump, the upstream pressure sensor creating an upstream pressure signal representative of the fluid pressure in the fluid tube during an infusion cycle, the upstream pressure signal including a section characteristic of the negative transient pressure;

a control module including a microprocessor which receives the upstream pressure signal from the upstream pressure sensor, the microprocessor programmed to create an upstream alarm signal if the section of the upstream pressure signal which is characteristic of the negative transient pressure is absent;

an alarm including circuitry configured to signal an upstream occlusion alarm when the upstream alarm signal is received from the control module.

14. A system as in claim 13 further comprising a downstream pressure sensor connected to the fluid tube downstream from the infusion pump, the downstream pressure sensor creating a signal representative of the fluid pressure in the fluid tube downstream from the pump during an infusion cycle, the microprocessor of the control module also receives the signal from the downstream pressure sensor, the microprocessor programmed to create a downstream alarm signal if downstream pressure signal exceeds a predetermined threshold, the alarm circuitry further configured to signal a downstream occlusion alarm when the downstream alarm signal is received from the control module.

15. A system for determining the fluid pressure in a fluid tube of an infusion system, the infusion system having a first and subsequent infusion cycles, the system comprising:

a sensor for partially compressing the fluid tube, the sensor configured to generate a signal characteristic of an estimated tube force prior to the first infusion cycle, and further configured to generate a signal characteristic of tube forces prior to subsequent infusion cycles; and a control module which receives the signals from the sensor, the control module stores the estimated tube force signal and includes a processor which is programmed to update the estimated tube force if the signals from any subsequent infusion cycle is less than the estimated tube force, the processor further programmed to calculate a fluid pressure as a function of the estimated tube force.

16. A system as in claim 15 wherein the processor is further programmed to generate an alarm signal, indicating an upstream or a downstream occlusion, as a function of the calculated fluid pressure.

17. A system as in claim 15 wherein the estimated tube force is updated as a function of a standard relaxation curve.

18. A system as in claim 15 wherein the estimated tube force is updated by subtracting a portion of subsequent force signals if those force signals are less than the most recently updated estimated tube force.

19. A system as in claim 15 wherein the estimated tube force is updated as a function of temperature.

* * * * *

UNITED STATES PATENT AND TRADEMARK OFFICE
CERTIFICATE OF CORRECTION

PATENT NO. : 5,695,473

DATED : December 9, 1997

INVENTOR(S) : Olsen

It is certified that error appears in the above-identified patent and that said Letters Patent is hereby corrected as shown below:

In column 9, line 29, insert —occlusion— after the word "upstream".

In column 9, line 29, delete "is pressure" after the word "upstream".

Signed and Sealed this

Twenty-eighth Day of July, 1998

Attest:

BRUCE LEHMAN

*Attesting Officer*   *Commissioner of Patents and Trademarks*